United States Patent [19]

VandenBerg

[11] Patent Number: Plant 7,753

[45] Date of Patent: Dec. 24, 1991

[54] CHRYSANTHEMUM PLANT NAMED MONTEREY

[75] Inventor: Cornelis P. VandenBerg, Salinas, Calif.

[73] Assignee: Yoder Brothers, Inc., Barberton, Ohio

[21] Appl. No.: 565,709

[22] Filed: Aug. 13, 1990

[51] Int. Cl.[5] ..... A01H 5/00

[52] U.S. Cl. ..... Plt./74

[58] Field of Search ..... Plt. 74, 74.1, 82.4, Plt./82.5

*Primary Examiner*—Howard J. Locker

*Attorney, Agent, or Firm*—Foley & Lardner

[57] ABSTRACT

A Chrysanthemum plant named Monterey particularly characterized by its flat capitulum form; daisy capitulum type; soft lavender pink ray floret color; diameter across face of capitulum of 83 to 95 mm. when fully opened when grown as a pinched spray pot mum; photoperiodic response to short days of 52 to 60 days; plant height of 18 to 30 cm. when grown as a pinched pot mum; and semi-spreading branching pattern, with 3 to 5 breaks per plant after pinch.

3 Drawing Sheets

The present invention comprises a new and distinct cultivar of Chrysanthemum, botanically known as *Dendranthema grandiflora,* and referred to by the cultivar name Monterey.

Monterey, identified as 86-420002, was originated from a cross made by Cornelis P. VandenBerg in a controlled breeding program in Salinas, Calif., in 1984.

The female parent of Monterey was an unnamed seedling identified as 81-565007, and described as a pink flat daisy pot spray mum having a flowering response to short days of 60 to 69 days under normal conditions, a height of 18 to 33 cm. with 13 to 17 long days after sticking unrooted cuttings and 1 to 3 applications of 2500 ppm B-9 SP, a semi-spreading breaking action with 4 to 6 breaks after pinch, and a diameter of capitulum of 83 to 95 mm. The female parent was discarded from the breeding program on Sept. 6, 1984.

The male parent of Monterey was also an unnamed seedling, identified as 80-347004, and described as a yellow flat daisy spray pot mum having a flowering response to short days of 54 to 59 days under normal conditions, a plant height of 28 to 36 cm. with 13 to 19 long days after sticking unrooted cuttings and 1 to 2 applications of 2500 ppm B-9 SP, a semi-spreading breaking action with 4 to 5 breaks per plant after pinch, and a diameter of capitulum of 83 to 89 mm. The male parent was discarded from the breeding program in September of 1985.

Monterey was discovered and selected as one flowering plant within the progeny of the stated cross by Cornelis P. VandenBerg in July 1986, in a controlled environment in Salinas, Calif.

The first act of asexual reproduction of Monterey was accomplished when vegetative cuttings were taken from the initial selection in September 1986 in a controlled environment in Salinas, Calif., by technicians working under the supervision of Cornelis P. VandenBerg.

Horticultural examination of controlled flowerings of successive plantings has shown that the unique combination of characteristics as herein disclosed for Monterey are firmly fixed and are retained through successive generations of asexual reproduction.

Monterey has not been observed under all possible environmental conditions. The phenotype may vary significantly with variations in environment such as temperature, light intensity and daylength.

The following observations, measurements and comparisons describe plants grown in Salinas, Calif. under greenhouse conditions which approximate those generally used in commercial greenhouse practice.

The following traits have been repeatedly observed and are determined to be basic characteristics of Monterey, which, in combination, distinguish this Chrysanthemum as a new and distinct cultivar:

1. Flat capitulum form.
2. Daisy capitulum type.
3. Soft lavender pink ray floret color.
4. Diameter across face of capitulum of 83 to 95 mm. when fully opened, when grown as a pinched spray pot mum.
5. Photoperiodic flowering response to short days of 52 to 60 days.
6. Plant height, with 15 to 18 long days after sticking unrooted cuttings, and with 1 to 2 applications of 2500 ppm B-9 SP, ranges from 18 to 30 cm. when grown as a pinched pot mum with 4 cuttings in a 15 cm. pot.
7. Branching pattern is semi-spreading, each plant having 3 to 5 laterals after pinch.

The accompanying photographic drawings show typical inflorescence and leaf characteristics of Monterey, with the colors being as nearly true as possible with illustrations of this type.

Sheet 1 is a color photograph of Monterey grown as a pinched spray pot mum with 4 cuttings in a 15 cm. pot.

Sheet 2 is a black and white photograph of three views of the inflorescence of Monterey.

Sheet 3 is a black and white photograph showing the upper and under sides of the leaves of Monterey at three stages of development (mature, intermediate and immature). Sheets 2 and 3 include a measuring tape in centimeters, thereby illustrating the flower and leaf dimensions.

Of the commercial cultivars known to the inventor, the most similar in comparison to Monterey is the cultivar Davis, disclosed in pending Plant patent application Ser. No. 388,894, now U.S. Plant Pat. No. 7,325. Reference is made to attached Chart A, which compares certain characteristics of Monterey to the same characteristics of Davis.

Similar traits are capitulum form and type. Plant height and number of breaks per plant after pinch is comparable for both cultivars, with Davis having a wider spread than Monterey. The ray floret color of Monterey is a soft lavender pink, while the ray floret color of Davis is a much darker red-purple. Flowering response of Monterey is slightly faster than that of Davis, and Monterey has a significantly larger flower diameter.

When compared with both parents, Monterey has a much faster flowering response than the female parent, with a similar flowering response to that of the male parent. The most significant difference between Monterey and both parents is the unique soft lavender pink ray floret color of Monterey, which color is also unique with respect to presently available commercial chrysanthemum cultivars.

In the following description color references are made to The Royal Horticultural Society Colour Chart. The color values were determined on plant material grown as a pinched spray pot mum in Salinas, Calif. on Mar. 22, 1990.

Classification:

*Botanical.*—*Dendranthema grandiflora* cv Monterey.

*Commercial.*—Daisy spray pot mum.

INFLORESCENCE

A. Capitulum:

*Form.*—Flat.

*Type.*—Daisy.

*Diameter across face.*—83 to 95 mm. when fully opened.

B. Corolla of ray florets:

*Color (general tonality from a distance of three meters).*—Soft lavender pink.

*Color.*—Upper surface: 75C to 75D. Under surface: 75D.

*Shape.*—Straight, pointed, slightly ribbed. Apex slightly indented.

C. Corolla of disc florets:

*Color (mature).*—12A.

*Color (immature).*—144C.

Reproductive organs:

*Androecium.*—Present on disc florets only; no pollen.

*Gynoecium.*—Present on both ray and disc florets.

PLANT

A. General appearance:

*Height.*—18 to 30 cm. when grown as a pinched pot mum in a 15 cm. pot with 15 to 18 long days after direct sticking of unrooted cuttings and 1 to 3 applications of 2500 ppm B-9 SP.

*Branching pattern.*—Semi-spreading, with 3 to 5 laterals after pinch.

B. Foliage:

*Color (upper surface).*—147A.

*Color (under surface).*—147B.

*Shape.*—See photograph.

CHART A

COMPARISON OF MONTEREY AND DAVIS

| CHARACTERISTIC | MONTEREY | DAVIS |
|---|---|---|
| Ray floret color | Soft lavender pink | Red-purple |
| Capitulum form and type | Flat daisy | Flat daisy |
| Diameter across face of capitulum | 83 to 95 mm. | 64 to 70 mm. |
| Flowering response | 52 to 60 days | 54 to 63 days |
| Plant height with 15 to 18 long days | 18 to 30 cm. | 18 to 25 cm. |
| Branching pattern | Semi-spreading 3 to 5 laterals | Spreading 3 to 6 laterals |

COMPARISONS MADE OF PLANTS GROWN AS PINCHED SPRAY POT MUMS IN SALINAS, CALIFORNIA

I claim:

1. A new and distinct Chrysanthemum plant named Monterey, as described and illustrated.

* * * * *

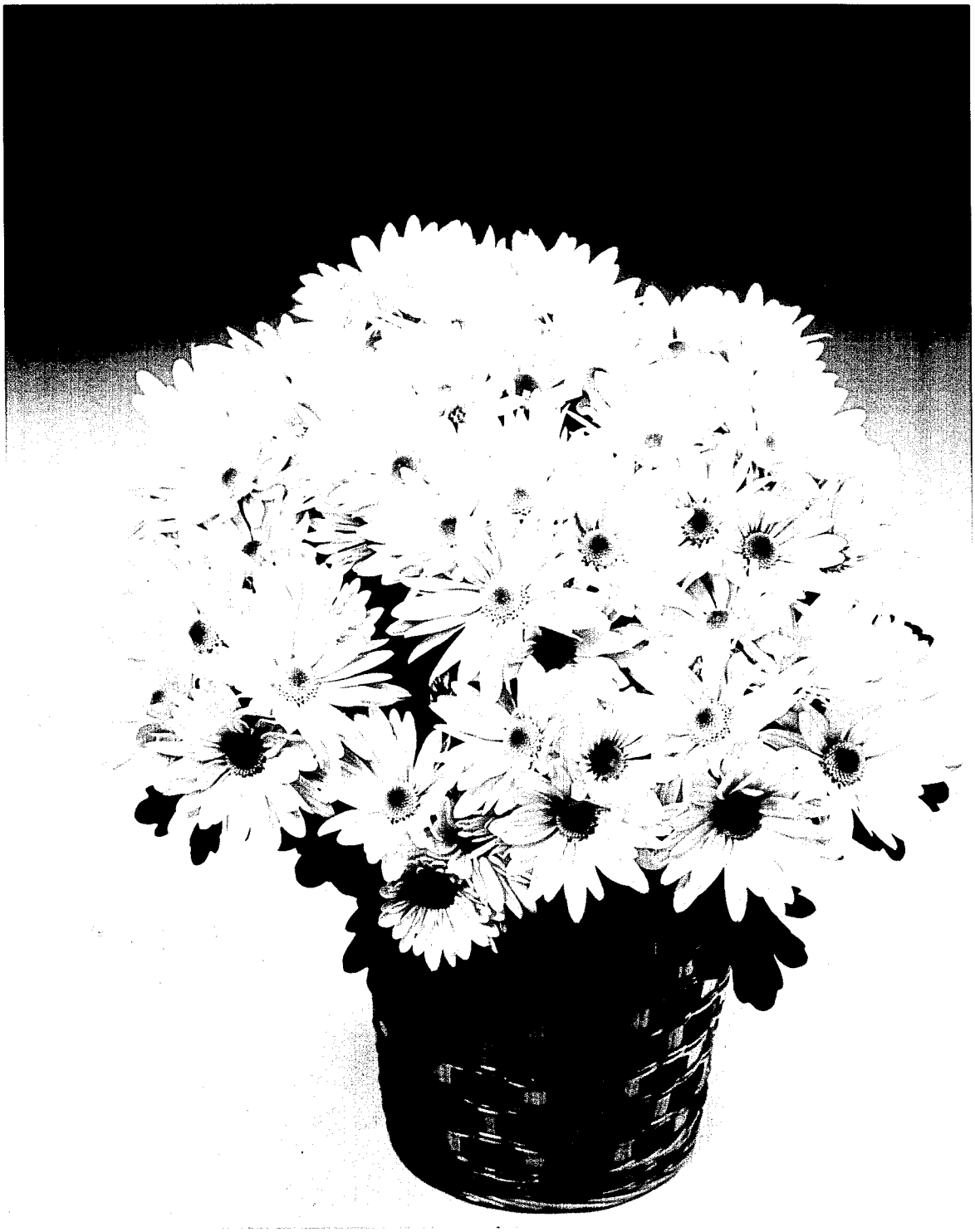

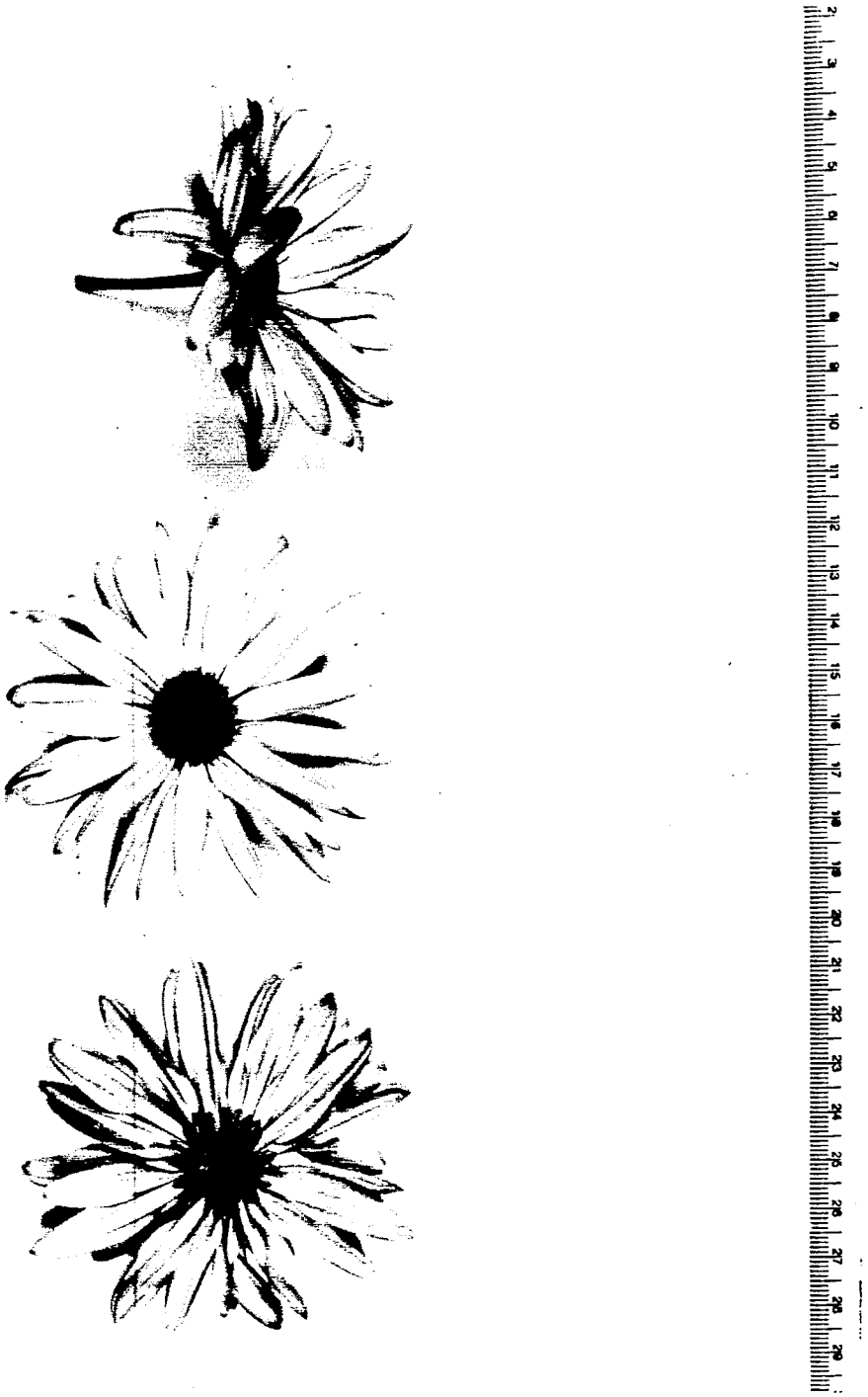

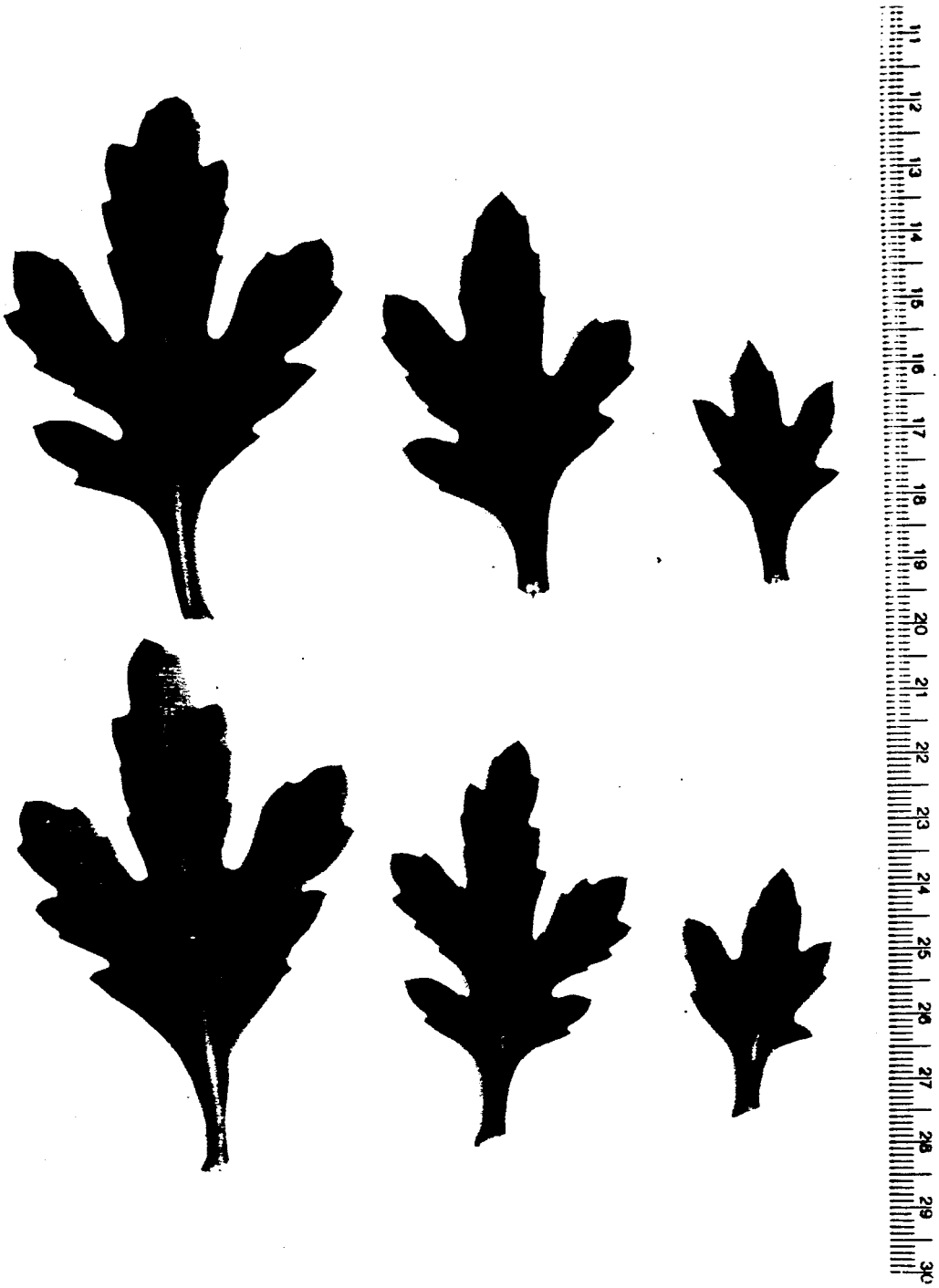
11
12
13
14
15
16
17
18
19
20
21
22
23
24
25
26
27
28
29
30